United States Patent [19]

Huang

[11] 4,376,721
[45] Mar. 15, 1983

[54] METHANOL SYNTHESIS CATALYST AND METHOD FOR ITS PREPARATION

[75] Inventor: Dinah C. Huang, Louisville, Ky.

[73] Assignee: Electric Power Research Institute, Inc., Palo Alto, Calif.

[21] Appl. No.: 286,204

[22] Filed: Jul. 22, 1981

[51] Int. Cl.³ .............................................. B01J 31/02
[52] U.S. Cl. .................................... 252/430; 252/463; 518/713
[58] Field of Search ................. 252/430, 463; 518/713

[56] References Cited

U.S. PATENT DOCUMENTS 4,111,847 9/1978 Stiles ................................... 252/463
4,279,781 7/1981 Dienes et al. ....................... 252/463

*Primary Examiner*—W. J. Shine
*Attorney, Agent, or Firm*—Flehr, Hohbach, Test, Albritton & Herbert

[57] ABSTRACT

A method is provided to promote, stabilize and strengthen metal catalysts used in the fluidized bed process for methanol synthesis which comprises the dipping of such catalysts into an alcoholic solution of metal alkoxide salt. The resulting improved catalyst is characterized by high density, low loss on attrition, and improved stability and catalytic activity.

27 Claims, No Drawings

METHANOL SYNTHESIS CATALYST AND METHOD FOR ITS PREPARATION

There has been recent interest in the development of methanol and higher alcohols as potential alternative energy resources which can be produced with synthesis gases from either coal gasification or natural gas reforming. Methanol is a particularly clean fuel, however further development in the technology of methanol synthesis is required to reduce costs in order to compete with other fuels. The low pressure methanol synthesis process involves the hydrogenation of carbon monoxide at 50–100 atm and 200°–300° C. in the presence of a copper/zinc oxide catalyst. Since the existence of a small percentage of carbon dioxide in the carbon monoxide feed stock has been found to be advantageous in preventing the catalytic deactivation, the two reactions commonly accepted as leading to the formation of methanol are as follows.

$$CO + 2H_2 \rightarrow CH_3OH$$
$$CO_2 + 3H_2 \rightarrow CH_3OH + H_2O$$

However it was found that under normal operating conditions, the second reaction involving carbon dioxide only contributes to a small percentage of the methanol product. The major reaction, hydrogenation of carbon monoxide into methanol is exothermic, however its equilibrium is less favorable at high temperatures. The reaction rate of the major methanol producing reaction is, therefore, limited by the effectiveness of heat dissipation. Therefore efforts have been made to maximize the conversion of methanol by operating the reaction under conditions which optimize both the reaction rate and the equilibrium balance.

In view of the difficulty in achieving efficient removal of reaction heat in uniform heating through the bed of a conventional fixed bed reactor, there has been developed a liquid phase methanol synthesis process which optimizes the methanol production through operation at higher conversions per pass. In this process, small catalyst particles are fluidized in inert mineral oil by upward feed gas. The intimate contact of the liquid and catalyst in this system, as well as the small sizes of catalyst particles, lessen the extent of local overheating. The reaction temperature is controlled by circulation of the liquid flow through a heat exchanger. Therefore by this process methanol production was increased by precise temperature control of an isothermic reactor operating at the optimized combination of both reaction rate and equilibrium balance.

However the process utilizing a fluidized bed reactor suffers from the disadvantage of not having a commercial catalyst which is particularly adapted for the process. Commercially available methanol synthesis catalysts in the form of large tablets are not suitable for a fluidized bed reactor because of the large fluidizing force which is required in the operation. Also the activity of such tablet catalysts is lower in a fluidized bed than a catalyst comprising smaller particles. Furthermore, a commercial catalyst powder, when formed into extrusions or spheres, are too weak in physical strength to endure the agitation in a fluidized bed to be of any practical use.

The problem with commercial catalyst strength in the use of a fluidized bed reactor rises from the fact that the catalyst contains a high percentage of copper oxide and zinc oxide. Upon reduction of the catalyst preceding the synthesis reaction, the major constituent of the catalyst particle, copper oxide, will be mostly reduced to metallic copper, leaving void spaces due to removal of the oxygen atoms in the catalyst matrices. This causes the weakness of mechanical strength in the reduced methanol synthesis catalyst. The mechanism of fluidizations suggests that catalyst particles in the liquid phase methanol process will best perform in the form of small extrusions or spheres. However the forming of commercial catalyst powder into extrusions or spheres further weakens the catalyst's mechanical strength. In addition the wetting preceding the extruding or during spheroidizing adds to the problem by adding extra void spaces in the catalyst particles. The result is that commercial catalyst powder which is used in the fluidized bed reactor process suffers from high attrition. It is therefore an object of the current invention to produce an attrition resistant methanol synthesis catalyst extruded in a size suitable for use in the liquid phase methanol synthesis process.

It has been found that catalytic compositions comprising a catalytically active metal, metal oxide, metal salt or a mixture thereof which catalyzes a chemical reaction to produce methanol in the presence of gaseous carbon monoxide, hydrogen and carbon dioxide and a solid carrier comprising an inert metal oxide or mixture of inert metal oxides, may be extruded, dipped in solutions containing metal alkoxides, followed by hydrolysis to produce densified catalysts which are attrition resistant when used in the fluidized bed process for methanol synthesis. It has also been found that the catalysts of the current invention have improved thermal stability and improved activity stability over extruded catalysts which have not been dipped in metal alkoxides.

It has been particularly found that catalysts compositions comprising a mixture of catalytically active copper oxide and zinc oxide on an aluminum carrier may be extruded and dipped in aluminum isopropoxide followed by hydrolysis, to produce attrition resistant methanol synthesis catalysts. While a mixture of copper oxide and zinc oxide is preferred, any catalytically active metal, catalytically active metal oxide or catalytically active metal salt may be used which is known to catalyze a chemical reaction to produce methanol in the presence of gaseous carbon monoxide, hydrogen and/or carbon dioxide. Examples of such catalytically active materials are copper oxide, barium oxide and zinc oxide.

Any metal oxide or mixture of metal oxides which is inert to the reaction of carbon monoxide, hydrogen and/or carbon dioxide to form methanol may be used as a solid carrier in the current invention. Examples of such solid carriers are aluminum oxide, zirconium oxide, chromium oxide, vanadium oxide, titanium oxide and a magnesium silicate, silicon oxide, or any mixture thereof.

The metal alkoxide salt in which the active metal composition and carrier are dipped forms a coating on each particle of catalyst. The inert metal alkoxide salts which may be used for said coatings are aluminum alkoxide and titanium alkoxide wherein the alkoxide anion contains from 1–10 carbon atoms. The preferred metal alkoxide salt is aluminum isopropoxide.

The catalyst precursors according to the current invention comprise a porous core, preferably extruded, consisting of the catalytically active metal oxide and solid carrier, surrounded by a coating of the metal alkoxide salt. The catalytic compositions according to the current invention are prepared from these precursors by contact with a hydrolyzing agent, preferably water, followed by calcining at a temperature of 100° F. to 600° F. Preferably, the precursor catalyst may be heated at about 500° F. for 1 to 4 hours, thereby causing the metal alkoxide coating to be converted to metal oxide and expelling alcohol. Therefore, a portion of the solid carrier of the catalytic composition comprises the metal oxide coating formed from calcination of the metal alkoxide. The catalytic composition may consist of from 90–50% active catalytic material and from 10–50% solid carrier. Preferably the active catalytic material is copper oxide and zinc oxide and the solid carrier is alumina. Based on weight, the composition may preferably contain from and about 10% to about 80% copper oxide, about 10% to about 80% zinc oxide and about 10% to about 50% alumina. A preferred range is from 15% to about 70% copper oxide and about 10% to about 65% zinc oxide. For example, said composition may consist of about 60–70% copper oxide, about 20–30% zinc oxide and about 10–15% alumina. As a specific example, the catalytic composition of the invention may consist of 65% copper oxide, 22% zinc oxide and 13% alumina.

The invention is further illustrated, but not intended to be limited to, the following examples.

EXAMPLE 1

A catalyst comprising 3:1 by weight copper oxide to zinc oxide mixtures on alumina supports were prepared by coprecipitation of the metal carbonates from the corresponding metal nitrate solutions in presence of the appropriate percentage by weight of alumina, followed by calcination to the metal oxides. To the powder of this metal oxide mixture was added 1% by weight methyl cellulose and the mixture was wetted and mixmulled for about one hour. The samples were then extruded through a laboratory hydraulic extruder with holes of 1/16 or 3/32 inch diameter and air dried. The extruded samples were then dipped either 2 to 5 times in aluminum isopropoxide dissolved in isopropyl alcohol. The dipped extrusions were dried at 150° F., then quickly dipped in water and redried at 150° F. and kept in a 500° F. oven for 2 hours. The catalysts prepared by this procedure are shown below in Table I.

TABLE I

DIPPED METHANOL SYNTHESIS CATALYST IN EXTRUSIONS

| Catalyst | Size | CuO/ZnO | % Al₂O₃ | Times Dipped |
|---|---|---|---|---|
| 1 | 1/16" | 3/1 | 13 | 2 |
| 2 | 3/32" | 3/1 | 12 | 5 |
| 3 | 1/16" | 3/1 | 13 | 5 |

EXAMPLE 2

The catalytic activities of these three dipped catalysts on the methanol synthesis from carbon monoxide and hydrogen were tested in side by side comparisons in a dual tube reactor. The activity of each catalyst was measured in average percentage of carbon monoxide conversion and crude methanol yield in kilograms per liter per hour, as shown in Table II below.

Catalyst No. 4 listed below in Table II is a 3-1 copper oxide: zinc oxide catalyst containing 10% alumina which was extruded through a 1/16" extruder, but not dipped in aluminum isopropoxide.

TABLE II

DIPPED CATALYST ACTIVITIES

| Catalyst | Average % CO Conversion | Crude Methanol Yield (kg/ltr/hr) |
|---|---|---|
| 1 | 36 | 0.266 |
| 2 | 43.6 | 0.313 |
| 3 | 39 | 0.316 |
| 4 | 33 | 0.258 |

EXAMPLE 3

The pore volumes of dipped catalyst were compared with the original catalyst 4. The pore volumes are shown below in Table III.

TABLE III

PORE VOLUMES OF DIPPED EXTRUSIONS

| Catalyst | Size | # of Times Dipped | Pore Vol., CC/G |
|---|---|---|---|
| 1 | 1/16" | 2 | 0.35 |
| 2 | 3/32" | 5 | 0.32 |
| 3 | 1/16" | 5 | 0.30 |
| 4 | 1/16" | 0 | 0.40 |

EXAMPLE 4

The physical properties of the dip extrusions were measured in terms of density, crush strength and percent loss on attrition.

The attrition test was run by placing the new catalyst or used catalyst in a steel drum mounted on an electric motor which rotates the drum. The drum is 12" in diameter, 8" in depth and has one 2" baffle. As the drum rotates, the catalyst rides up on the baffle and drops back to the bottom. In this test the drum was rotated at 72 rpm for a period of 30 minutes. Then the catalyst is screened over a 20 mesh screen and the weight is compared to the original weight of material charged into the drum. The weight loss is reported as weight percentage loss on attrition.

TABLE IV

PHYSICAL PROPERTIES OF DIPPED EXTRUSIONS

| Catalyst | Density × 15 (gm/15 ml) | Crush Strength lbs/mm | % Loss On Attrition/ New | % Loss On Atttrition/ Used |
|---|---|---|---|---|
| 1 | 12.8 | 1.8 | 1.4 | 3.0 |
| 2 | 15.5 | — | — | 25.2 |
| 3 | 15.6 | 2.2 | 1.4 | 8.0[1] |
| 4 | 12.0 | 1.0 | 4.0 | 3.1 |

[1] Attrition test was performed after subjecting catalyst to 200 hrs. of thermostability tests up to 556° F.

EXAMPLE 5

A thermostability test was performed with the dipped and original undipped catalyst loaded side by side in the dual tube reactor. After each increment in reaction temperature, the catalyst activities were checked under the normal testing conditions. The results of this test are given below in Table V. It can be seen from these data that dipped catalyst 3 exhibits improved thermostability over undipped catalyst 4.

TABLE V

COMPARISON IN THERMOSTABILITES OF DIPPED AND UNDIPPED EXTRUSIONS

| | CATALYST #3 (DIPPED) | | | CATALYST #4 (UNDIPPED) | | |
|---|---|---|---|---|---|---|
| Days on Stream | Inlet Temp. °F. | Hot Spot Temp. °F. | % CO Conversion | Inlet Temp. °F. | Hot Spot Temp. °F. | #CO Conversion |
| 1 | 410 | 432 | 39.3 | 411 | 431 | 33.6 |
| 2 | 415 | 437 | 38.5 | 416 | 436 | 35.0 |
| 3 | 456 | 481 | | 456.5 | 475.5 | |
| 4 | 412 | 430.5 | 37.5 | 413 | 427.5 | 30.5 |
| 5 | 495.5 | 520.5 | | 496.5 | 518 | |
| 6 | 414.5 | 431 | 36.5 | 415 | 427 | 25.3 |
| 7 | 533 | 556 | | 534 | 555 | |
| 8 | 415 | 429.5 | 29.0 | 416.5 | 424.5 | 17.2 |

EXAMPLE 6

Since in the liquid phase methanol synthesis process the catalytic particles are fluidized in the medium of mineral oil, the catalysts were subjected to an oil attrition test designed to check the effect of the presence of oil during attrition. An enclosed metal tube of $1\frac{3}{8}'' \times 5\frac{3}{4}''$ was filled with 20 mils catalyst and 100 mils normal hexane. The tube was then closed with about 50 mils empty space. The tube was rotated perpendicular to its axis at 72 rpm for 30 minutes causing the catalyst particles to be agitated through the tube in the turbulence of air and liquid. Table VI below lists the used catalytic attrition for catalyst #3 from both dry (from Table IV above) and wet attrition tests. It can be seen that the attrition was much less severe in the oil test as compared to the dry attrition situation. Catalyst #3 had a clear supernatant liquid after the attrition test.

TABLE VI

COMPARISON IN USED ATTRITION FROM DRY AND WET TESTS

| Catalyst | Dry Test % Loss On Attrition (used) | Oil Test % Loss On Attrition Reduced |
|---|---|---|
| 3 | 8.0[1] | 0.24 |

What is claimed is:

1. A composition comprising a catalytically active metal, metal oxide, metal salt or a mixture thereof which catalyzes a chemical reaction to produce methanol in the presence of gaseous carbon monoxide, hydrogen and carbon dioxide; a solid carrier comprising a catalytically inert metal oxide or a mixture of catalytically inert metal oxides; and a catalytically inert metal alkoxide coating wherein said alkoxide contains 1-10 carbon atoms.

2. A composition according to claim 1 wherein said composition comprises porous particles having a core consisting of said catalytically active metal, metal oxide, metal salt or mixture thereof and said solid carrier; wherein said particles have a coating consisting of said inert metal alkoxide.

3. A composition according to claim 2 wherein said core consists of said catalytically active metal, metal oxide, metal salt or mixture thereof and said solid carrier.

4. A composition according to claim 3 wherein said core consists of a mixture of catalytically active metal oxides and a solid carrier.

5. A composition according to claim 4 wherein said catalytically active metal oxides are selected from the group consisting of copper oxide, zinc oxide, and barium oxide; said solid carrier is selected from the group consisting of aluminum oxide, zirconium oxide, chromium oxide, vanadium oxide, silicon oxide, titanium oxide, magnesium silicate, or a mixture thereof; and said coating of inert metal alkoxide is selected from the group consisting of aluminum alkoxide and titanium alkoxide.

6. A composition according to claim 5 wherein said mixture of catalytically active metal oxides consist of copper oxide and zinc oxide and said solid carrier is aluminum oxide.

7. A composition according to claim 6 wherein said coating of inert metal alkoxide is aluminum alkoxide.

8. A composition according to claim 7 wherein said aluminum alkoxide is aluminum isopropoxide.

9. A composition according to claim 8 wherein said core is extruded.

10. In a method for preparing a catalytic composition comprising a catalytically active metal, metal oxide, metal salt or a mixture thereof which catalyzes a chemical reaction to produce methanol in the presence of gaseous carbon monoxide, hydrogen and carbon dioxide; and a solid carrier comprising a catalytically inert metal oxide or a mixture of catalytically inert metal oxides; the improvement comprising immersing said catalytic composition in a solution containing an inert metal alkoxide, drying said catalytic composition, immersing said catalytic composition in water, and heating said catalytic composition at a temperature from about 100° F. to 600° F.

11. A method according to claim 10 wherein said catalytic composition is extruded prior to being immersed into said solution containing metal alkoxide.

12. A method according to claim 11 wherein said catalytic composition consists of a mixture of catalytically active metal oxides and said solid carrier.

13. A method according to claim 12 wherein said catalytically active metal oxides are selected from the group consisting of copper oxide, zinc oxide, and barium oxide; said solid carrier is selected from the group consisting of aluminum oxide, zirconium oxide, chromium oxide, vanadium oxide, silicon oxide, titanium oxide, magnesium silicate or a mixture thereof; and said metal alkoxide is selected from the group consisting of aluminum and titanium alkoxide.

14. A method according to claim 13 wherein said mixture of catalytically active metal oxides consists of copper oxides and zinc oxide and said solid carrier is aluminum oxide.

15. A method according to claim 14 wherein said inert metal alkoxide is aluminum alkoxide.

16. A method according to claim 15 wherein said aluminum alkoxide is aluminum isopropoxide.

17. A catalytic composition comprising a catalytically active material selected from the group consisting of a metal, metal oxide, a metal salt or a mixture thereof which catalyzes a chemical reaction to produce methanol in the presence of gaseous carbon monoxide, hydrogen and carbon dioxide; and a solid carrier comprising a catalytically inert material selected from the group consisting of a metal oxide or a mixture of catalytically inert metal oxides; wherein a portion of said solid carrier is provided by immersing particles comprising said catalytically active material and inert material into a solution containing a metal alkoxide, removing said particles from said solution, drying said particles, immersing said particles in water, removing said particles from said water and subjecting said particles to a temperature of about 100° F. to 600° F.

18. A catalytic composition according to claim 17 wherein said composition comprises porous particles having a core consisting of said catalytically active material and said inert material; wherein said particles have a coating consisting of said inert material.

19. A catalytic composition according to claim 18 wherein said core is an extruded composition consisting of said catalytically active material and said inert material.

20. A catalytic composition according to claim 19 wherein said core consists of a mixture of catalytically active metal oxides and said inert material.

21. A catalytic composition according to claim 20 wherein said catalytically active metal oxides are selected from the group consisting of copper oxide, zinc oxide and barium oxide; and said inert material is selected from the group consisting of aluminum oxide, zirconium oxide, chromium oxide, vanadium oxide, silicon oxide, titanium oxide, magnesium silicate or a mixture thereof.

22. A catalytic composition according to claim 21 wherein said mixture of catalytically active metal oxides consist of copper oxide and zinc oxide and said inert material is aluminum oxide.

23. A catalytic composition according to claim 22 wherein said metal alkoxide is aluminum alkoxide.

24. A catalytic composition according to claim 23 wherein said aluminum alkoxide is aluminum isopropoxide.

25. A catalytic composition according to claim 24 consisting of from about 10% to about 80% copper oxide, about 10% to about 80% zinc oxide and about 10% to about 50% aluminum oxide.

26. A catalytic composition according to claim 25 consisting of from about 15% to about 70% copper oxide and about 10% to about 65% zinc oxide.

27. A catalytic composition according to claim 26 consisting of from about 10% to 15% aluminum oxide.

* * * * *